United States Patent
Richardson

(10) Patent No.: US 11,045,084 B2
(45) Date of Patent: Jun. 29, 2021

(54) METHOD AND SYSTEM FOR DETECTION AND TREATMENT OF AUTISM SPECTRUM DISORDERS AND OTHER DISORDERS

(71) Applicant: Megan Lorane Richardson, Las Cruces, NM (US)

(72) Inventor: Megan Lorane Richardson, Las Cruces, NM (US)

(73) Assignee: Megan Lorane Richardson, Las Cruces, NM (US)

( * ) Notice: Subject to any disclaimer, the term of this patent is extended or adjusted under 35 U.S.C. 154(b) by 31 days.

(21) Appl. No.: 15/208,604

(22) Filed: Jul. 12, 2016

(65) Prior Publication Data

US 2018/0070810 A1    Mar. 15, 2018

Related U.S. Application Data

(60) Provisional application No. 62/191,554, filed on Jul. 13, 2015.

(51) Int. Cl.
| | |
|---|---|
| *A61B 3/02* | (2006.01) |
| *A61B 5/00* | (2006.01) |
| *A61B 5/12* | (2006.01) |
| *A61B 3/00* | (2006.01) |
| *A61B 5/16* | (2006.01) |

(52) U.S. Cl.
CPC .............. *A61B 3/02* (2013.01); *A61B 3/0041* (2013.01); *A61B 5/4076* (2013.01); *A61B 5/12* (2013.01); *A61B 5/168* (2013.01)

(58) Field of Classification Search
CPC ....... A61B 3/02; A61B 3/0041; A61B 5/4076; A61B 5/4088; A61B 5/12; A61B 5/16; A61B 5/162; A61B 5/168
See application file for complete search history.

(56) References Cited

U.S. PATENT DOCUMENTS

2015/0379877 A1* 12/2015 Edgin ................... A61B 5/16
434/236

OTHER PUBLICATIONS

Occelli et al., "The takete-maluma phenomenon in autism spectrum disorders", Perception, vol. 42, Issue 2, pp. 233-241, 2013.*
Nielsen et al., "The Sound of Round: Evaluating the Sound-Symbolic Role of Consonants in the Classic Takete-Maluma Phenomenon", Canadian Journal of Experimental Psychology, Vo. 65, No. 2, pp. 115-124, 2011.*
Neurotypical Wikipedia definition. https://en.wikipedia.org/wiki/Neurotypical.*
Drijvers et al. ("Sound-Symbolismis Disrupted in Dyslexia: Implications for the Role of Cross-Modal AbstractionProcesses", 37th AnnualMeeting of the Cognitive Science Society, pp. 602-607, Jul. 2015) (Year: 2015).*
D'Onofrio, A, (2012). Refining bouba-kiki: Phonetic detail and object dimensionality in sound-shape corraspondences. J. Acoust. Soc. Am., 132(3), 1968.
Maurer, D., Pathman, T., & Mondloch, C. (2006). The shape of boubas: sound-shape correspondences in toddlers and adults, Developmental Sciences, 9(3), 316-322.
Nielsen, A., & Rendall, D. (2011), The sound of round: Evaluating the sound symbolic role of consonants in the classic Takete-Maluma phenomenon. Canadian Journal of Experimental Psychology/Revue Canadienna de Psychologie Expérimentala, 65(2), 115-124.
Oberman, L., & Ramachandran, V. (2008), Preliminary evidence for deficits in multisensory integration in autism spectrum disorders: The mirror neuron hypothesis. Social Neuroscience, 3(3-4), 348-355.
Occelli, V., Esposito, G., Venuti, P., Arouino, G., & Zampini, M. (2013), The takete-maluma phenomenon in autism spectrum disorders. Perception, 42, 233-241.
Köhler, W. (1929). Gestalt Psychology, New York: Oversight.

* cited by examiner

*Primary Examiner* — Devin B Henson

(57) ABSTRACT

A system and method of detecting and treating autism spectrum disorders and other neurological conditions uses associations of stimuli in one mode, such as images, with stimuli in another mode, such as sounds.

15 Claims, No Drawings

METHOD AND SYSTEM FOR DETECTION AND TREATMENT OF AUTISM SPECTRUM DISORDERS AND OTHER DISORDERS

CROSS-REFERENCE TO RELATED APPLICATIONS

This application claims the benefit of provisional patent application Ser. No. 62/191,554, filed 2015 Jul. 13 by the present inventor, which is incorporated by reference.

BACKGROUND

The bouba-kiki effect (also known as the takete-maluma effect) is a cross-modal perceptual phenomenon whereby most people associate jagged, "spiky" or "sharp" shapes with "jagged"-, "spiky"- or "sharp"-sounding utterances, and rounded, smooth shapes with "rounded"- or "smooth"-sounding utterances. "Jaggedness"/"smoothness" of utterances is associated with the presence of stops/continuants, voicelessness/voice of phones, and other phonological elements. The effect is seen in nonautistic persons of a wide range of ages (including babies a few months old), reading skill levels (including non-literacy), and language backgrounds. Individuals with any of a range of autism spectrum disorders, however, are much less likely than others to exhibit this phenomenon. Individuals with dyslexia exhibit the phenomenon more weakly than others.

Prior Art—Patents

There are no prior patents that appear relevant.

Prior Art—Nonpatent Literature Documents

D'Onofrio, A. (2012). Refining bouba-kiki: Phonetic detail and object dimensionality in sound-shape correspondences. *J. Acoust. Soc. Am.,* 132(3), 1968.

Maurer, D., Pathman, T., & Mondloch, C. (2006). The shape of boubas: sound-shape correspondences in toddlers and adults. *Developmental Science,* 9(3), 316-322.

Nielsen, A., & Rendall, D. (2011). The sound of round: Evaluating the sound-symbolic role of consonants in the classic Takete-Maluma phenomenon. *Canadian Journal of Experimental Psychology/Revue Canadienne de Psychologie Expérimentale,* 65(2), 115-124.

Oberman, L., & Ramachandran, V. (2008). Preliminary evidence for deficits in multisensory integration in autism spectrum disorders: The mirror neuron hypothesis. *Social Neuroscience,* 3(3-4), 348-355.

Occelli, V., Esposito, G., Venuti, P., Arduino, G., & Zampini, M. (2013). The takete-maluma phenomenon in autism spectrum disorders. *Perception,* 42, 233-241.

The literature does not propose the use of the phenomenon to detect, screen for, nor diagnose any condition; it does note the differential appearance of the phenomenon in people with certain disabilities and notes regularities in cross-modal associations where they do appear. These regularities suggest various means for classifying certain stimuli as kiki or bouba.

The present invention, in one or more of its embodiments, is a novel method and system for testing to detect, diagnose, and reduce effects of autism spectrum disorders and other disorders.

Advantages

The advantages of one or more embodiments include, without limitation, that the system minimizes the communicative, motor, and social skills required of the subject to participate in the test or training; that it minimizes the skills and training required of a test administrator; that it minimizes the equipment required for administration of the test; and that it minimizes the time spent testing. One or more aspects allow for heretofore-impracticable screening of larger numbers of subjects, such as whole kindergarten classes. The present invention produces objective data which can be used in diagnosing autism, where today, subjective data is often used. Certain embodiments can be used with subjects of a wide range of ages, reading abilities, language backgrounds, and cultural backgrounds. One or more aspects can produce data for diagnosing dyslexia and other disabilities. In addition to increasing ease and objectivity, one or more aspects also feature the potential to dramatically reduce costs for these kinds of services. Some embodiments of the present invention are quick, procedurally and technologically simple tests to detect autism and other disorders.

DETAILED DESCRIPTION—FIRST EMBODIMENT

In some embodiments the subject is asked to make associations between images and pseudowords to determine the extent to which the subject exhibits the bouba-kiki effect.

Certain embodiments of the present invention use drawings of characters on physical cards of paper or other material as the image stimuli. In some embodiments, these characters are imaginary animals.

The images are previously categorized as rounded/smooth ("bouba-like") or as jagged/"spiky"/"sharp" ("kiki-like"), either in experiment with nonautistic, nondyslexic subjects, and/or based on the scientific literature on perception and on the bouba-kiki effect.

In some embodiments, the other set of stimuli are sound stimuli in the form of invented names. The names are pseudo-words (pronounceable combinations of syllables that have no meaning in the subject's language(s)). The names are composed of syllables previously categorized as "jagged"/"spiky"/"sharp" ("kiki-like") or as "rounded"/ "smooth" ("bouba-like"), either in experiment by non-autistic, non-dyslexic subjects, and/or based on the scientific literature on phonology and on the bouba-kilci effect.

In such embodiments, the upper limit on the number of names is determined by the number of predeterminedly kiki and bouha syllables, and the chosen syllable limit (how long we decide the names should be). The number of images required is therefore, in such embodiments, a function of the number of names as well as the number of responses needed to interpret the test. Syllable combinations that have meaning in language(s) to which the subject has been exposed should then eliminated from the list.

Operation—First Embodiment

In some embodiments, during the test, the subject is asked to choose a name for a given image, or to choose an image for a given name, from options given by a test administrator. The subject is asked to make several image/name pairings; the exact number of questions may vary according to the type of subject. In some embodiments, this takes the form of the test administrator asking the subject what the character on the card should be called, and giving two options, a kiki-type name and a houba-type name.

In some embodiments, names are written for the test administrator so as to likely be read in a way that fits the appropriate kiki or bouba category despite variations in pronunciation. In some embodiments, International Phonetic Alphabet spellings of the names are also provided to test administrators.

In some embodiments, an experimentally tested, specific protocol for eliciting responses is given to test administrators.

Responses can be given by the subject verbally, gesturally, or by other means depending on the needs of the subject and on the protocol used.

In some embodiments, the degree to which the subject's responses exhibit the bouba-kiki effect (the degree of match with expected, neurotypical, bouba-kiki style responses) is determined. In some embodiments, this measure is used to determine the probability that the subject has an autism spectrum disorder, based on information derived from results of previous tests of subjects whose autistic status had been otherwise established.

Additional Embodiments—Description

There are various possibilities with regard to materials and perceptual modes used. Some embodiments use abstract designs on cards. Some embodiments use software to present the stimuli. Images can be displayed on a screen, or projected onto a screen or wall.

In various embodiments, pseudoword stimuli may be given to the subject as recorded audio played on a computer or audio device, or in writing, in spelled sign language, etc., as needed. To standardize pronunciation, audio of the preferred pronunciation of name stimuli can be made available to test administrators in another medium. Sounds other than speech can be used in some embodiments, for example, music.

Some embodiments can use an object such as a card with a raised design, or a three-dimensional object, possibly made with a three-dimensional printer based on a provided template. These embodiments can be used with visually impaired subjects and others.

In some embodiments, stimuli can be presented, and/or responses recorded, by software embodied in a computer instead of by a human test administrator.

Additional Embodiments—Operation

Variations on protocol are possible for the test, such as varying the number of options, or the mode of the stimuli.

Variations on the information to be derived are also possible, given established data on cross-modal perceptual phenomena. For example, calibrating tests can be done to find atypical:typical response ratios suggestive of dyslexia. Such information may become available for other disabilities, especially reading difficulties, in future.

Other embodiments employ other perceptual modes.

Some embodiments of the system can also be used to train a person on cross-modal associations. The sets of stimuli described above are paired in these embodiments such that "matching" stimuli are displayed together (that is, stimuli of different modes predetermined to belong to certain categories of stimuli that tend to be perceived as cross-modally associated in nonautistic and nondyslexic humans are displayed together). In some embodiments, recorded video and audio are stored on media to be played in a projector, such as those used to project images on the ceiling above a baby's bed. Said recording displays "matched" stimuli together, such as animations of bouba images with a bouba soundtrack alternating with kiki animations with kiki soundtrack. In other embodiments, the same materials prepared for testing can be used for training. For example, the card set and name list described in the first embodiment can be used in this manner; thus the same physical device can leverage the same psycholinguistic phenomena to a different end in this method.

CONCLUSIONS, RAMIFICATIONS, AND SCOPE

The reader will thus see that some embodiments of the system provide a novel way to test for autism spectrum disorders and other disorders, some embodiments provide a novel way to train people with autism and other disorders on cross-modal perceptions, and some embodiments provide both.

For ramifications, please see Additional Embodiments, above.

While the foregoing written description of the invention enables one of ordinary skill in the field (such as cognitive psychologists and educational diagnosticians with knowledge of linguistics) to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

What is claimed is:

1. A method comprising:
   presenting at least one from pluralities of kiki-type and bouba-type objects or images to a testee;
   presenting at least one from pluralities of kiki-type and bouba-type audio or written items to said testee;
   associating, by selection by the testee, objects or images presented for identification with presented audio or written items;
   scoring of the selection using a scoring protocol to determine one of a plurality of point values;
   repeating these prior steps until said plurality of point values are aggregated to determine an overall score; and
   comparing said overall score to one or more standardized score ranges to determine the presence or severity of pathology.

2. The method of claim 1,
   wherein said pluralities of objects for identification comprise a plurality of pictures on physical cards.

3. The method of claim 1,
   wherein said pluralities of objects for identification comprise a plurality of raised designs on physical cards.

4. The method of claim 1,
   wherein said pluralities of objects for identification comprise a plurality of three-dimensional objects.

5. The method of claim 1,
   wherein said plurality of kiki-type audio or written items and said plurality of bouba-type audio or written items comprise a plurality of pseudowords known in the art.

6. The method of claim 1,
   wherein scores are compared to a standardized score range indicating typical and atypical autism-spectrum scores.

7. The method of claim 1,
   wherein scores are compared to a standardized score range indicating typical and atypical dyslexia-spectrum scores.

8. The method of claim 1,
wherein scores are compared to a standardized score range indicating typical and atypical normal-spectrum scores.

9. The method of claim 1, further comprising:
a software application; and
a computing system;
wherein said presented audio items from said pluralities of kiki-type items and of bouba-type items are presented to a testee via said application on an audio output of said computing system.

10. The method of claim 9,
wherein said presented objects or images from said pluralities of objects or images for identification are presented to a testee via said application on a visual output of said computing system.

11. The method of claim 9,
wherein the testee's selected responses are input to said computing system.

12. The method of claim 1; further comprising:
repeating of said prior steps to determine a progression of overall scores.

13. A system comprising:
a plurality of kiki-type images;
a plurality of bouba-type images;
a plurality of kiki-type audio recordings;
a plurality of bouba-type audio recordings;
a software application; and
a computing system
adapted to display, via said application, at least one image from said plurality of kiki-type images to a trainee on a visual output of said computing system while simultaneously playing an audio recording from said plurality of kiki-type audio recordings on an audio output of said computing system, and
to display, via said application, at least one image from said plurality of bouba-type images to the trainee on a visual output of said computing system while simultaneously playing an audio recording from said plurality of bouba-type audio recordings on an audio output of said computing system; and
to repeat this audio-visual display process during the session.

14. A system comprising:
a plurality of kiki-type visible or tactile items for presentation to a testee;
a plurality of bouba-type visible or tactile items for presentation to a testee;
a plurality of kiki-type audio items or written items for presentation to the testee;
a plurality of bouba-type audio items or written items for presentation to the testee;
a protocol for presenting the items and prompting the testee to associate said presented items;
a scoring protocol;
and one or more standardized score ranges giving scores suggestive of some neurological condition.

15. A method comprising:
displaying, via a software application, at least one image from a plurality of kiki-type images to a trainee on a visual output of a computing system, while simultaneously playing an audio recording from a plurality of kiki-type audio recordings on an audio output of said computing system, and
displaying, via a software application, at least one image from a plurality of bouba-type images to a trainee on a visual output of a computing system, while simultaneously playing an audio recording from a plurality of bouba-type audio recordings on an audio output of said computing system; and
repeating this audio-visual display process during a training session.

* * * * *